(12) United States Patent
Sato

(10) Patent No.: US 11,195,597 B2
(45) Date of Patent: Dec. 7, 2021

(54) METHOD AND DEVICE FOR CALCULATING ACID DISSOCIATION CONSTANT, AND PROGRAM

(71) Applicant: FUJITSU LIMITED, Kawasaki (JP)

(72) Inventor: Hiroyuki Sato, Yokohama (JP)

(73) Assignee: FUJITSU LIMITED, Kawasaki (JP)

( * ) Notice: Subject to any disclaimer, the term of this patent is extended or adjusted under 35 U.S.C. 154(b) by 575 days.

(21) Appl. No.: 15/858,438

(22) Filed: Dec. 29, 2017

(65) Prior Publication Data

US 2018/0121632 A1 May 3, 2018

Related U.S. Application Data

(63) Continuation of application No. PCT/JP2015/070625, filed on Jul. 17, 2015.

(51) Int. Cl.
| | |
|---|---|
| *G01N 33/48* | (2006.01) |
| *G01N 33/50* | (2006.01) |
| *G16C 20/30* | (2019.01) |
| *G16C 20/90* | (2019.01) |
| *G16B 99/00* | (2019.01) |

(52) U.S. Cl.
CPC ............ *G16C 20/30* (2019.02); *G16B 99/00* (2019.02); *G16C 20/90* (2019.02)

(58) Field of Classification Search
CPC ......... G16C 20/30; G16C 20/90; G16B 99/00
See application file for complete search history.

(56) References Cited

U.S. PATENT DOCUMENTS

| | | |
|---|---|---|
| 7,006,921 B1 | 2/2006 | Xing et al. |
| 2014/0229148 A1 | 8/2014 | Sato et al. |

FOREIGN PATENT DOCUMENTS

| | | |
|---|---|---|
| JP | 2004-77405 | 3/2004 |
| JP | 2014-157020 | 8/2014 |

OTHER PUBLICATIONS

Beroza et al. Calculation of amino acid pKas in a protein from a continuum electrostatic model: Method and sensitivity analysis. Journal of Computational Chemistry, vol. 17, pp. 1229-1244. (Year: 1996).*

(Continued)

*Primary Examiner* — Russell S Negin
(74) *Attorney, Agent, or Firm* — Staas & Halsey LLP

(57) ABSTRACT

A calculation method of acid dissociation constant, including: calculating the acid dissociation constant using function that uses index value determined based on electron density between two atoms in calculation target molecule and coefficient value determined based on types of two elements of set of the two atoms, wherein when the calculation target molecule includes at least one amino group and dissociation of hydrogen atom from one amino group in the at least one amino group is calculated, the function further uses second electron density of nitrogen atom in the one amino group not related to bond between the nitrogen atom and another atom, bond distance between the nitrogen atom and the hydrogen atom, and molecular orbital energy of the calculation target molecule, wherein the calculation method is method for calculating acid dissociation constant in dissociation of the hydrogen atom from the calculation target molecule using computer.

10 Claims, 6 Drawing Sheets

(56) References Cited

OTHER PUBLICATIONS

Jahanbakhsh Ghasemi, et al., "QSPR study for estimation of acidity constants of some aromatic acids derivatives using multiple linear regression (MLR) analysis," Journal of Molecular Structure: THEOCHEM, vol. 805, Issues 1-3, Elsevier, Mar. 28, 2007, pp. 27-32**.

I. Mayer, "Bond Order and Valence Indices: A Personal Account," Journal of Computational Chemistry, Wiley Online Library, vol. 28, Issue 1, Jan. 2007, pp. 204-221**.

Elena Soriano, "Computational determination of $pK_a$ values. A comparison of different theoretical approaches and a novel procedure," Journal of Molecular Structure (Theochem), vol. 684, Issues 1-3, Elsevier, Sep. 24, 2004, pp. 121-128**.

Gloria A.A. Saracino, et al. "Absolute $pK_a$ determination for carboxylic acids using density functional theory and the polarizable continuum model," Chemical Physics Letters, vol. 373, Issues 3-4, Elsevier, May 20, 2003, pp. 411-415**.

Junming Ho, et al., "A universal approach for continuum solvent $pK_a$ calculations: are we there yet?," Theor Chem Acc, 2010, pp. 3-21.

Mario J. Citra, "Estimating the $pK_a$ of Phenols, Carboxylic Acids and Alcohols From Semi-Empirical Quantum Chemical Methods," Chemosphere, vol. 38, No. 1, 1999, pp. 191-206.

International Search Report dated Aug. 25, 2015, in corresponding International Patent Application No. PCT/JP2015/070625.

Written Opinion of the International Searching Authority dated Aug. 25, 2015 in corresponding International Patent Application No. PCT/JP2015/070625.

Kido, et al., "Systematic Assessment on Aqueous $pK_a$ and $pK_b$ of an Amino Acid Base on RISM-SCF-SEDD Method: Toward First Principles Calculations," International Journal of Quantum Chemistry, vol. 112, No. 1, published online Jan. 18, 2011, XP55488790, pp. 103-112**.

Extended European Search Report dated Jul. 10, 2018, in corresponding European Patent Application No. 15898886.5, 11 pgs.

* cited by examiner

METHOD AND DEVICE FOR CALCULATING ACID DISSOCIATION CONSTANT, AND PROGRAM

CROSS-REFERENCE TO RELATED APPLICATION

This application is a continuation application of International Application PCT/JP2015/070625 filed on Jul. 17, 2015 and designated the U.S., the entire contents of which are incorporated herein by reference.

FIELD

The embodiments discussed herein relate to a method for calculating an acid dissociation constant, a device for calculating an acid dissociation constant, and a program for calculating an acid dissociation constant.

BACKGROUND

PKa is a constant representing an equilibrium state of acid dissociation (i.e., acidity), and is used as an index for determining the presence of protons ($H^+$) that are important in a chemical reaction performed in biomolecules. Accordingly, various estimation methods of pKa have been studied. The estimation methods are roughly classified into two types. One type of methods are methods based on the thermodynamic theory (see, for example, Junming Ho, Michelle L. Coote, "A universal approach for continuum solvent pKa calculations: are we there yet?" Theor Chem Acc, 2010, pp. 3-21). The other type of methods are methods where approximation of pKa is performed with a function using physical property values as variables (see, for example, Jahanbakhsh Ghasemi, Saadi Saaidpour, Steven D. Brown, "QSPR study for estimation of acidity constants of some aromatic acids derivatives using multiple linear regression (MLR) analysis", Journal of Molecular Structure, THEOCHEM, 2007, pp. 27-32, and Mario J. Citra, "ESTIMATING THE pKa OF PHENOLS, CARBOXYLIC ACIDS AND ALCOHOLS FROM SEMI-EMPIRICAL QUANTUM CHEMICAL METHODS", Chemosphere, 1999, Vol. 38, No. 1, pp. 191-206).

According to the former method, calculation can be performed according to the theory. According to the latter method, basically high-speed estimation can be performed.

According to the method based on the thermodynamic theory, however, pKa is largely influenced by the number or positions of water molecules present around a target molecule, and moreover highly accurate calculation needs to be performed to obtain an excellent result. As a result, it is still impossible to estimate pKa at high speed. Accordingly, it is difficult to apply the method based on the thermodynamic theory for macromolecules or screening of a large volume of data.

Moreover, various physical properties values have been studied in the method where approximation of pKa is performed with a function using physical property values as variables, in order to realize highly accurate estimation. For example, there is a method where distances between charges or OH are used as variables associated with a hydrogen atom (H) dissociated as a proton and an oxygen atom (O) directly bonded to H. However, with such variables, a separate function formula is necessary depending on types of acid of a target molecule. Moreover, highly accurate results cannot be obtained with all of the function formulae.

Therefore, it is difficult to apply the above-described method for a novel molecule synthesized.

Therefore, the present inventors proposed a technology associated with an estimation value of pKa, where the technology could be applied for macromolecules, screening of a large volume of data, and novel molecules synthesized (see, for example, Japanese Patent Application Laid-Open (JP-A) No. 2014-157020).

SUMMARY

The disclosed calculation method of an acid dissociation constant is a method for calculating an acid dissociation constant in dissociation of a hydrogen atom from a calculation target molecule using a computer. The calculation method includes calculating the acid dissociation constant using a function that uses an index value determined based on electron density between two atoms in a calculation target molecule and a coefficient value determined based on types of two elements of a set of the two atoms, wherein, when the calculation target molecule includes at least one amino group and dissociation of a hydrogen atom from one amino group in the at least one amino group is calculated, the function further uses second electron density of a nitrogen atom in the one amino group where the second electron density is not related to a bond between the nitrogen atom and another atom, a bond distance between the nitrogen atom and the hydrogen atom, and molecular orbital energy of the calculation target molecule.

The disclosed program is a program for executing a calculation method of an acid dissociation constant in dissociation of a hydrogen atom from a calculation target molecule, and the calculation method includes calculating the acid dissociation constant using a function that uses an index value determined based on electron density between two atoms in a calculation target molecule and a coefficient value determined based on types of two elements of a set of the two atoms, wherein, when the calculation target molecule includes at least one amino group and dissociation of the hydrogen atom from one amino group in the at least one amino group is calculated, the function further uses second electron density of a nitrogen atom in the one amino group where the second electron density is not related to a bond between the nitrogen atom and another atom, a bond distance between the nitrogen atom and the hydrogen atom, and molecular orbital energy of the calculation target molecule.

The disclosed calculation device of an acid dissociation constant includes a memory unit. The calculation device is configured to calculate an acid dissociation constant in dissociation of a hydrogen atom from a calculation target molecule, the memory unit includes, as data, an index value determined based on electron density between two atoms in a calculation target molecule and a coefficient value determined based on types of two elements of a set of the two atoms, and wherein, when the calculation target molecule includes at least one amino group and dissociation of a hydrogen atom from one amino group in the at least one amino group is calculated, the memory unit further includes second electron density of a nitrogen atom in the one amino group where the second electron density is not related to a bond between the nitrogen atom and another atom, a bond distance between the nitrogen atom and the hydrogen atom, and molecular orbital energy of the calculation target molecule.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

First, as the related art, an estimation method of an acid dissociation constant pKa is described.

Figure 1:
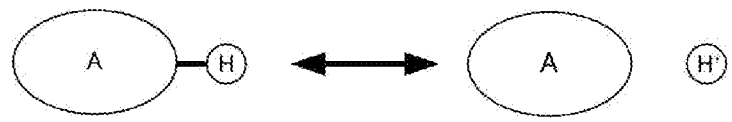
FIG. 1 is a view for describing an acid dissociation constant pKa.

FIG. 1 is a view for describing an acid dissociation constant pKa. As illustrated in FIG. 1, pKa is a constant representing an equilibrium state of acid dissociation, and is represented by the following mathematical equation (1) and equilibrium equation (1).

$$pK_a = -\log K_a \text{ with the } proviso \text{ that} \quad \text{Mathematical Equation (1)}$$
$$K_a = \frac{[A^-][H^+]}{[AH]}$$

$$AH_{[aq]} \longleftrightarrow A^-_{[aq]} + H^+_{[aq]} \quad \text{Equilibrium Equation (1)}$$

In the mathematical equation (1) and equilibrium equation (1), AH is an acid, $A^-$ is a conjugate base of AH, and $H^+$ is a proton.

The pKa is an index determining the presence of a proton ($H^+$) that is important in a chemical reaction performed within a biomolecule.

The present inventors have proposed a technology that is associated with an estimation value of pKa, and can be applied for a macromolecule, screening of a large volume of data, and a novel molecule synthesized (see, JP-A No. 2014-157020). According to the proposed technology associated with an acid dissociation constant pKa of a molecule, high-speed and highly accurate estimation of pKa in proton dissociation from OH in oxoacid is realized by using an index based on electron density of a bond between atoms regardless of a type of the molecule.

However, the present inventors have continuously performed researches further and have found that the estimation accuracy of pKa lowers according to the above-described technology in case of proton dissociation of amine.

The present inventors have studied a cause for the above-mentioned problem. As a result, the present inventors have found that the pKa estimation accuracy is decreased by influences of (1) a change in reactivity due to a change in steric hindrance before and after proton dissociation of amine, and (2) a change in reactivity due to a change in resonance stabilization of an electron structure before and after proton dissociation of amine.

The present inventors have continuously performed studies based on the insights above and accomplished the disclosed technology.

(Calculation method of acid dissociation constant, calculation device of acid dissociation constant, and program)

The disclosed calculation method of an acid dissociation constant is performed using a computer.

The calculation method of an acid dissociation constant calculates an acid dissociation constant in dissociation of a hydrogen atom from a calculation target molecule.

Examples of the calculation target molecule include oxoacid and amine.

According to the calculation method of an acid dissociation constant, a high-speed and highly accurate calculation can be performed not only on oxoacid and primary amine, but also secondary amine, tertiary amine, and aromatic amine.

The disclosed program is a program for executing calculation of an acid dissociation constant in dissociation of a hydrogen atom from a calculation target molecule.

According to the calculation method of an acid dissociation constant, the acid dissociation constant is calculated using a function.

With the program, calculation of the acid dissociation constant is executed using a function.

The function uses an index value and a coefficient value.

The index value is determined based on electron density between two atoms of the calculation target molecule.

The coefficient value is determined based on types of two elements of a set of the two atoms.

When the calculation method of an acid dissociation constant uses the calculation target molecule including at least one amino group and calculates dissociation of the hydrogen atom in one amino group among the at least one amino group, the function further uses electron density, a bond distance, and molecular orbital energy.

The electron density is second electron density [may be referred to as "electron density ($D_{Nfree}$)" hereinafter] of a nitrogen atom of the one amino group, where the second electron density is not related to a bond between the nitrogen atom and another atom.

The bond distance is a bond distance between the nitrogen atom and the hydrogen atom.

The molecular orbital energy is molecular orbital energy of the calculation target molecule.

In the present specification, a hydrogen atom that is a calculation target of an acid dissociation constant may be referred to as a "target proton." The hydrogen atom in the one amino group corresponds to a target proton.

The calculation device of an acid dissociation constant includes a memory unit.

The memory unit includes the following data.

The index value

The coefficient value

When the calculation target molecule includes at least one amino group and dissociation of the hydrogen atom in one amino group among the at least one amino group is calculated, moreover, the memory unit further includes the following data.

Figure 2:
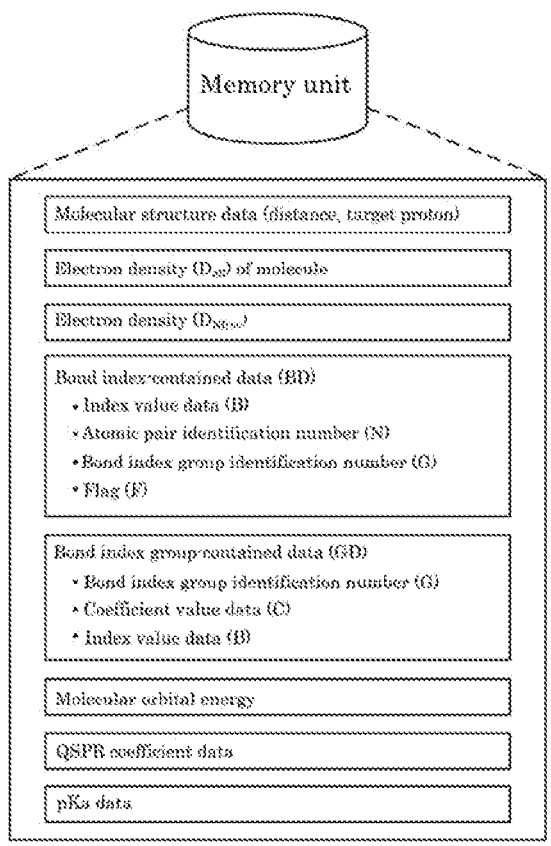
FIG. 2 is a view illustrating one example of a memory unit.

The electron density ($D_{Nfree}$)
The bond distance
The molecular orbital energy One example of the memory unit is illustrated in FIG. 2.

The memory unit illustrated in FIG. 2 includes the following data. The data of the memory unit is data used for calculating an acid dissociation constant of an amino group of amine.

Molecular structure data
Electron density ($D_{all}$) of a molecule
Electron density ($D_{Nfree}$)
Bond index-contained data (BD)
Bond index group-contained data (GD)
Molecular orbital energy
QSPR coefficient data
pKa data The bond index-contained data (BD) includes the following data.

Index value data (B)
Atomic pair identification number (N)
Bond index group identification number (G)
Flag (F)

The bond index group-contained data (GD) includes the following data.

Bond index group identification number (G)
Coefficient value data (C)
Index value data (B)

Note that, QSPR is the abbreviation for quantitative structure property relationship, and the QSPR coefficient data is a coefficient related to a numerical quantity for determining a degree of contribution of the numerical quantity representing a structure in QSPR.

Other data is described later.

Since the calculation method of an acid dissociation constant uses the electron density ($D_{Nfree}$), the bond distance, and the molecular orbital energy as variables of the function, calculation accuracy of an acid dissociation constant of amine can be increased with maintaining calculation accuracy of an acid dissociation constant of oxoacid, compared to the technology disclosed in JP-A No. 2014-157020.

<Index Value>

The index value is determined based on electron density between two atoms of the calculation target molecule.

For example, the index value ($B_{ab}$) is determined by electron density matrix ($D_{ij}$) between the two atoms (a and b). For example, the mathematical equation for the index value ($B_{ab}$) is represented by the following mathematical equation (2).

$$B_{ab} = \sum_{i \in a} \sum_{j \in b} |D_{ij}|^2 \quad \text{Mathematical equation (2)}$$

Note that, a set of the two atoms may be referred to as an "atomic pair" hereinafter.

When the data structure is described, moreover, the index value may be referred to as "index value data (B)."

The electron density matrix ($D_{ij0}$) is obtained by determining electron density of the whole calculation target molecule.

The index value may be set with all of sets of arbitrary selected two atoms (atomic pairs) of the calculation target molecule, and is preferably set with the following atomic pairs in order to accelerate calculation speed without lowering calculation accuracy.

Figure 3:
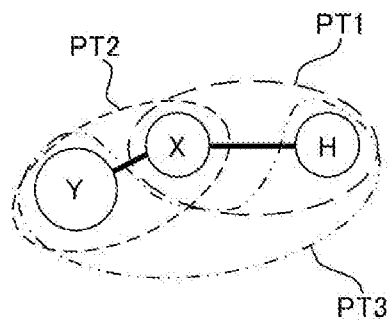
FIG. 3 is a view for describing an atomic set.

Set of the hydrogen atom and a first atom directly bonded to the hydrogen atom
Set of the first atom and a second atom (excluding the hydrogen atom) directly bonded to the first atom
Set of the hydrogen atom and the second atom The atomic pairs are described with reference to FIG. 3.

Set of a target proton <H> and an atom <X> directly bonded to the target proton <H>. Specifically, a set of a target proton <H> and an atom <X> (pair type PT1).

Set of an atom <X> directly bonded to the target proton <H> and an atom <Y> directly bonded to the atom <X> but being other than the target proton <H>. Specifically, a set of an atom <X> and an atom <Y> (pair type PT2).

Set of the target proton <H> and an atom <Y> directly bonded to the atom <X> but being other than the target proton <H>. Specifically, a set of a target proton <H> and an atom <Y> (pair type PT3).

Note that, the atom <X> (first atom) is an atom directly bonded to a target proton <H>. When the calculation target molecule is oxoacid, for example, X is an oxygen atom (O). When the calculation target molecule is amine, X is a nitrogen atom (N).

Moreover, the atom <Y> (second atom) is an atom directly bonded to the atom <X>, but is an atom other than a target proton <H>.

Since a target proton, an atom (first atom) directly bonded to the target proton, and an atom (second atom) directly bonded to the atom are considered and a set of two atoms (atomic pair) is selected from the above-mentioned atoms when the index value is determined, and the index value is used for calculation, as described above, the faster calculation can be realized.

For example, electron density of the calculation target molecule can be determined by molecular orbital calculation. The molecular orbital calculation is not particularly limited and may be appropriately selected depending on the intended purpose. Examples of the molecular orbital calculation include molecular orbital calculation according to molecule orbital calculations according to a molecular orbital method. Examples of the molecular orbital calculations include nonempirical molecular orbital calculations (ab initio molecular orbital calculation), and semiempirical molecular orbital calculations.

Examples of a methodology of the nonempirical molecular orbital calculation include the Hartree-Fock method, and the electron correlation method.

Examples of a methodology of the semiempirical molecular orbital calculation include CNDO, INDO, AM1, and PM3.

Examples of a program of the nonempirical molecular orbital calculation include Gaussian03, GAMESS, ABINIT-MP, and Protein DF.

Examples of a program of the semiempirical molecular orbital calculation include MOPAC.

<Coefficient Value>

The coefficient value is determined based on types of two elements of a set of the two atoms.

The coefficient value is a numerical value used for weighting the index value.

For example, the coefficient value is determined based on preliminary calculation of pKa.

Hereinafter, the coefficient value may be referred to as coefficient value data (C) and the index value may be referred to as index value data (B).

In the function, the product of the index value and the coefficient value is preferably used. Specifically, weighting is preferably performed on the index value using the coefficient value.

The calculation device of an acid dissociation constant preferably further includes a calculation unit configured to calculate an acid dissociation constant using the data in the memory unit, and a product of the index value and the coefficient value is preferably calculated in the calculation unit.

The coefficient value is preferably set for each of the following sets.
One set of the hydrogen atom and the first atom.
Sets of the first atom and the second atom, and the number of the sets is the number of types of the second atom.
Sets of the hydrogen atom and the second atom, and the number of the sets is the number of types of the second atom.

For example, sets of the second atom (atomic pairs) are divided into groups based on types of elements constituting the atomic pairs. Then, a coefficient value is set for each group.

For example, the grouping is performed in the following manner.

A set of a target proton and an atom directly bonded to the target proton forms one group itself. Specifically, the pair type PT1 per se forms one group.

The pair type PT2 is grouped by the number of types of an element of Y.

The pair type PT3 is grouped by the number of types of an element of Y.

Note that, a set of atoms in one group when a coefficient value is set may be referred to as an "element pair" hereinafter.

The memory unit includes, for example, bond index-contained data (BD) for each of atomic pairs used for calculation.

Each bond index-contained data (BD) includes the following data corresponding to an atomic pair.
Index value data (B) set per atomic pair
Atomic pair identification number (N) (a different number for each atomic pair) given to each atomic pair to identify the atomic pair
Bond index group identification number (G) (a different number for each group) given to each group to identify the group formed with the types of elements constituting the atomic pair
Flag (F) for classifying atomic pairs The memory unit includes, for example, a bond index group-contained data (GD) per group.

Each bond index group-contained data (GD) includes the following data corresponding to the group.
Bond index group identification number (G) (a different number for each group)
Coefficient value data (C) set per element pair
Index value data (B) corresponding to the atomic pairs belonging to the group Since the bond index-contained data (BD) and the bond index group-contained data (GD) are included as a data structure, the faster calculation can be realized.

For example, weighting of the index value with the coefficient value is performed as follows.
Bond index group-contained data (GD) belonging to the bond index group identification number (G) is represented as follows.

$GD[G]$

Index value data (B) of bond index group-contained data (GD) belonging to bond index group identification number (G) is represented as follows.

$GD[G] \to B$

Bond index-contained data (BD) belonging to atomic pair identification number (N) is represented as follows.

$BD[N]$

Index value data (B) of BD[N] is represented as follows.

$BD[N] \to B$

Flag (F) of BD[N] is represented as follows.

$BD[N] \to F$

Bond index group identification number (G) to which BD[N] belongs is represented as follows.

$BD[N] \to G$

Coefficient value data (C) belonging to bond index group identification number (G) is represented as follows.

$GD[G] \to C$

Index value data (B) of bond index group-contained data (GD) is determined as follows.

$GD[G] \to B = \Sigma_{(N \in G)} BD[N] \to B$

Then, weighting of index value data (B) with coefficient value data (C) is represented as follows.

$GD[G] \to C*GD[G] \to B$

When the calculation target molecule includes at least one amino group and dissociation of the hydrogen atom in one amino group among the at least one amino group is calculated, the following second electron density [electron density $(D_{Nfree})$], a bond distance, and molecular orbital energy are further used in the function.

In the function, the second electron density, the bond distance, and the molecular orbital energy form linear combination.

In the calculation device of an acid dissociation constant, a linear combination is preferably formed with the second electron density, the bond distance, and the molecular orbital energy in the calculation unit.

<Second Electron Density [Electron Density $(D_{Nfree})$]>

The second electron density is electron density $(D_{Nfree})$ of a nitrogen atom of the one amino group and is electron density that is not related to bond between the nitrogen atom and another atom.

For example, the electron density $(D_{Nfree})$ is obtained in the following manner.

Electron density $(D_{all})$ of the whole calculation target molecule is determined. Next, elements with which a nitrogen atom directly bonded to a target proton is associated are extracted from the obtained electron density $(D_{all})$. Next, an element associated with a bond between the nitrogen atom and another atom is excluded from the extracted elements. As a result, the electron density $(D_{Nfree})$ is obtained.

For example, $D_{Nfree}$ can be determined using the following mathematical equation (3).

$$D_{Nfree} = \sum_{i,j \in N} D_{ij}^2 - \sum_X B_{NX} \qquad \text{Mathematical equation (3)}$$

In the mathematical equation (3), $D_{ij}$ represents elements (electron density matrix) with which a nitrogen atom directly bonded to a target proton among the electron density, i represents a line component of the electron density matrix and j represents a column component of the electron density matrix, B represents an index value, and X represents another atom bonded to a nitrogen atom (N).

<Bond Distance>

The bond distance is a bond distance (R) between the nitrogen atom and the hydrogen atom (target proton).

For example, the bond distance can be determined by molecular orbital calculation.

<Molecular Orbital Energy>

Molecular orbital of the molecular orbital energy ($E_{mo}$) is not particularly limited and may be appropriately selected depending on the intended purpose. The molecular orbital is preferably the highest occupied molecular orbital and the lowest unoccupied molecular orbital because the highest occupied molecular orbital and the lowest unoccupied molecular orbital are largely related to reactivity of the amine.

A calculation method of the molecular orbital energy is not particularly limited and may be appropriately selected depending on the intended purpose. Examples of the calculation method include quantum mechanics (QM) calculations. Examples of the quantum mechanics calculations include molecule orbital calculations according to a molecular orbital method. Examples of the molecular orbital calculations include nonempirical molecular orbital calculations (ab initio molecular orbital calculation), and semiempirical molecular orbital calculations. Examples of a methodology and program of each calculation method includes the above-described methodologies and programs.

<Others>

In the calculation method of an acid dissociation constant, at least one of heat of formation of the calculation target molecule, heat of formation of a molecule formed by releasing a target proton from the calculation target molecule (may be referred to as "proton-released molecule" hereinafter), electron density ($D_{Nfree}$) of the proton-released molecule, and molecular orbital energy of the proton-released molecule is preferably further used because calculation accuracy is further improved.

The above-mentioned parameters are preferably weighted with appropriately set coefficients.

Examples of the function when the acid dissociation constant is calculated include the following function.

In the following function, the bond distance (R), the molecular orbital energy ($E_{mo}$), and the electron density ($D_{Nfree}$), each of which is weighted with an appropriate coefficient, form a linear combination.

$$pK_a \cong f\left(\sum_X a_{NX} B_{NX}, \sum_X a_{HX} B_{HX}, \right.$$
$$\left. a_R R_{NH} + a_E E_{MO} + a_D \left(\sum_{i,j \in N} D_{ij}^2 - \sum_X B_{NX}\right)\right)$$

In the formula above, a is a coefficient value.

Figure 4:
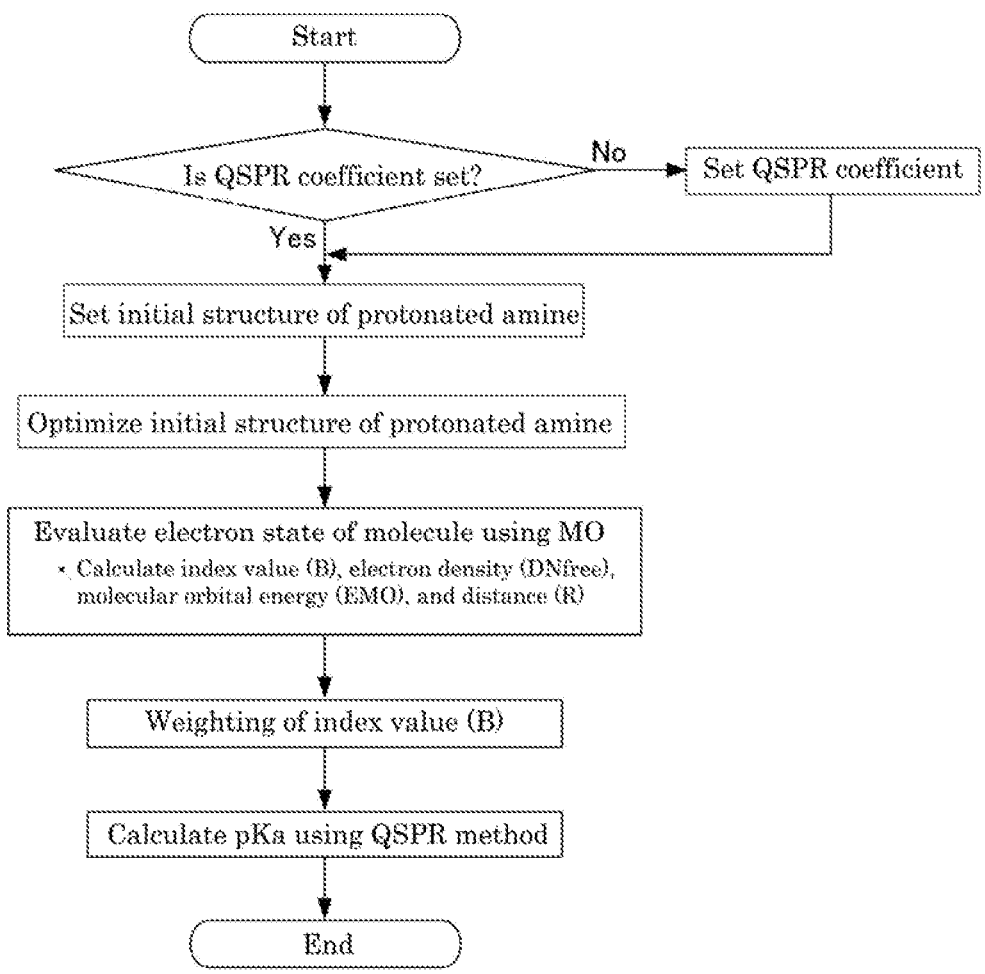
FIG. 4 is a flowchart describing one example of a calculation method of an acid dissociation constant.

A flow chart of one example of the calculation method of an acid dissociation constant is depicted in FIG. 4.

The calculation method according to the flow chart is explained hereinafter. In the flow chart, protonated amine is used as a calculation target molecule.

First, a QSPR coefficient is set.

Next, an initial structure of a protonated amine is set.

Next, the structure of the protonated amine is optimized. The optimization of the structure is performed according to a typical structure optimization calculation method. It is often a case that a bond length, a bond angle, a dihedral angle, etc., are chemically unnatural in the initial structure. Therefore, the structure optimization calculation is performed to correct the distortion of the structure of the molecule. For example, the structure optimization calculation can be performed by using a typical molecular orbital calculation program.

Next, a molecular orbital calculation (MO) is performed to evaluate an electron state of a molecule and the following items are calculated.

Index value (B) per atomic pair
Electron density ($D_{Nfree}$)
Molecular orbital energy ($E_{MO}$) (e.g., LUMO)
Bond distance (R)

Next, weighting of the index value (B) is performed with a coefficient value (C).

$$(GD[G] \to C^* GD[G] \to B)$$

Next, pKa is calculated using the QSPR method.

One example of the calculation method of an acid dissociation constant is described hereinafter.

Figure 5A:
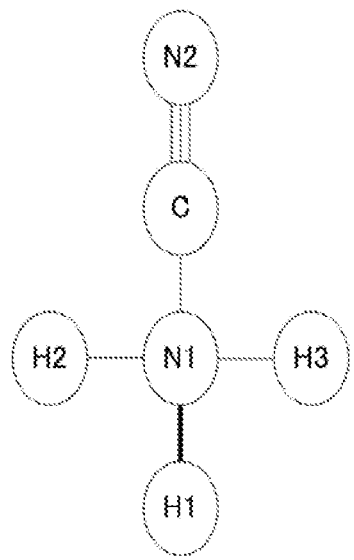
FIG. 5A illustrates amine (protonated amine) that is a calculation target in one example of a calculation method of an acid dissociation constant.

In the example, pKa of amine illustrated in FIG. 5A is calculated. In the case where there are several identical elements in amine, a number is provided to each atom. Such amine is protonated amine.

<O>

As a preparation stage, a coefficient value is set for subjects below.

Element pair
Bond distance (R) between a target proton <H1> and a nitrogen atom <N1>
Electron density (Q) of the nitrogen atom <N1>, where the electron density is not related to a bond between the nitrogen atom <N1> and another atom
Molecular orbital energy of the amine
Heat of formation before and after proton dissociation

<I>

Molecular orbital calculation of the amine is performed.

<II>

Bond index group-contained data (GD) and bond index-contained data (BD) of the amine are generated. Specifically, the following processes <<II-1>> to <<II-5>> are performed.

<<II-1>>

The atomic pair identification number (N) of the bond index-contained data (BD) is set in a manner that a different number is given per pair of the target proton <H1> and another atom. Similarly, a pair of the nitrogen atom <N1> directly bonded to the target proton <H1> and another atom is set in a manner that a different number is given per pair. The bond index-contained data (BD) is divided per atomic pair according to the atomic pair identification number (N).

The atomic pair identification number (N) of the amine is set as follows.

N1-C:1
N1-H1:2
N1-H2:3
N1-H3:4
N1-N2:5
H1-C:6
H1-H2:7
H1-H3:8
H1-N2:9

<<II-2>>

The bond index group identification number (G) of the bond index group-contained data (GD) and the bond index group identification number (G) of the bond index-contained data are set by grouping the atomic pairs classified by the atomic pair identification number (N). At the time of grouping, atomic pairs among the atomic pairs classified by the atomic pair identification number (N) are compared, and the atomic pairs having the identical elements constituting the atomic pair are set in the same group. However, the atomic pair of the target proton <H1> and the nitrogen atom <N1> directly bonded to the target proton <H1> is set as an independent group different from a pair of another nitrogen atom or a hydrogen atom.

The bond index group-contained data (GD) can be classified into groups of atomic pairs by the bond index group identification number (G). Moreover, the bond index group identification number (G) is set as BD[N]→G in the data structure of the bond index-contained data (BD), and BD and GD[G] can be linked. As a result, the calculation speed is improved.

The bond index group identification number (G) of the amine is set as follows.
N1-H1:1
N1-H:2
N1-C:3
N1-N:4
H1-H:5
H1-C:6
H1-N:7

<<II-3>>

Index value data (B) is obtained based on the electron density of the result of the molecular orbital calculation of the amine. Each obtained index value data (B) is set to each BD[N] (BD[N]→B).
BD[1]→B=$B_{N1-C}$
BD[2]→B=$B_{N1-H1}$
BD[3]→B=$B_{N1-H2}$
BD[4]→B=$B_{N1-H3}$
BD[5]→B=$B_{N1-N2}$
BD[6]→B=$B_{H1-C}$
BD[7]→B=$B_{H1-H2}$
BD[8]→B=$B_{H1-H3}$
BD[9]→B=$B_{H1-N2}$ BD[N]→G is as follows.
BD[1]→G=3
BD[2]→G=1
BD[3,4]→G=2
BD[5]→G=4
BD[6]→G=6
BD[7,8]→G=5
BD[9]→G=7

Moreover, a flag (F) of the atomic pair is set to each BD[N] (BD[N]→F). The atomic pair of the target proton <H1> and the nitrogen atom <N1> and other atomic pairs are classified by the flag.
BD[1,3,4,5,6,7,8,9]→F=2
BD[2]→F=1

<<II-4>>

A sum of BD[N]→B is obtained per group of the atomic pairs and the result is set to GD[G]→B.
GD[1]→B=BD[2]→B
GD[2]→B=BD[3]→B+BD[4]→B
GD[3]→B=BD[1]→B
GD[4]→B=BD[5]→B
GD[5]→B=BD[7]→B+BD[8]→B
GD[6]→B=BD[6]→B
GD[7]→B=BD[9]→B

<<II-5>>

The coefficient value data (C) for an element pair that is already set is set for an atomic pair GD[G]→C.

<III>

Weighting of index value data (B) is performed with coefficient value data (C).

GD[G]→B*GD[G]→C

<IV>

Weighting of a bond distance (R) between a target proton <H1> and a nitrogen atom <N1> is performed with a coefficient $C_R$ for the bond distance (R).

R*$C_R$

<V>

Weighting of electron density ($Q_{1N1}$) that is not related to a bond between a nitrogen atom and another atom is performed with a coefficient ($C_{1N1}$) for the electron density.

$Q_{1N1}*C_{1N1}$

<VI>

Weighting of molecular orbital energy ($E_{LUMO1}$) of the lowest unoccupied molecular orbital is performed with a coefficient ($C_{LUMO1}$) for molecular orbital energy.

$E_{LUMO1}*C_{LUMO1}$

<VII>

Weighting is optionally performed also on other data.

Weighting of the heat of formation ($E_{HoF1}$) of the amine is performed with a coefficient ($C_{HoF1}$) associated with heat of formation.

$E_{HoF1}*C_{HoF1}$

Figure 5B:
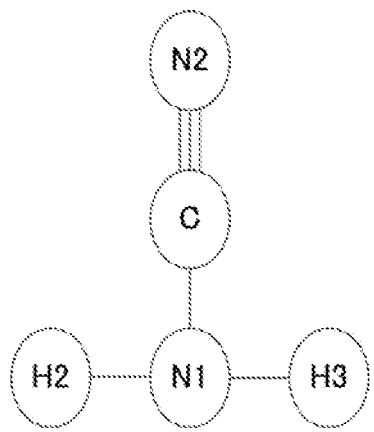
FIG. 5B is amine (amine after deprotonation) that is a calculation target in one example of a calculation method of an acid dissociation constant.

In the molecule (Molecule 2 in FIG. 5B) after deprotonation of the amine, weighting of the electron density ($Q_{2N1}$) of the nitrogen atom <N1> not related to the bond of the nitrogen atom <N1> and another atom is performed with a coefficient ($C_{2N1}$) associated with electron density.

$Q_{2N1}*C_{2N1}$

In Molecule 2, weighting of the molecular orbital energy ($E_{HOMO2}$) of the highest occupied molecular orbital is performed with a coefficient ($C_{HOMO2}$) associated with molecular orbital energy.

$E_{HOMO2}*C_{HOMO2}$

Weighting of heat of formation ($E_{HoF2}$) of Molecule 2 is performed with a coefficient ($C_{HoF2}$) relative to the heat of formation.

$E_{HoF2}*C_{HoF2}$

<VIII>

The pKa value is calculated using the data above.

The mathematical equation using the data of <I> to <VI> is the following mathematical equation (4).

$$pka = C_0 + \Sigma_G GD[G] \rightarrow B*GD[G] \rightarrow C + C_R*R + C_{1N1}*Q_{1N1} + C_{LUMO1}*E_{LUMO1} \quad \text{Mathematical Equation (4)}$$

Moreover, the mathematical equation to which the data of <VII> is further added is presented below. In the following mathematical equation (5), electron density ($Q_{2N1}$) of a molecule after proton dissociation, molecular orbital energy, and heat of formation of the molecule before and after proton dissociation are considered. Therefore, calculation accuracy is further improved.

$$pka = C_0 + \Sigma_G GD[G] \rightarrow B*GD[G] \rightarrow C + C_R*R + C_{1N1}*Q_{1N1} + C_{LUMO1}*E_{LUMO1} + C_{2N1}*Q_{2N1} + C_{HOMO2}*E_{HOMO2} + C_{HoF1}*E_{HoF1} + C_{HoF2}*E_{HoF2} \quad \text{Mathematical Equation (5)}$$

In the mathematical equations (4) and (5), $C_0$ is a constant term of the equation of QSPR.

Figure 6:
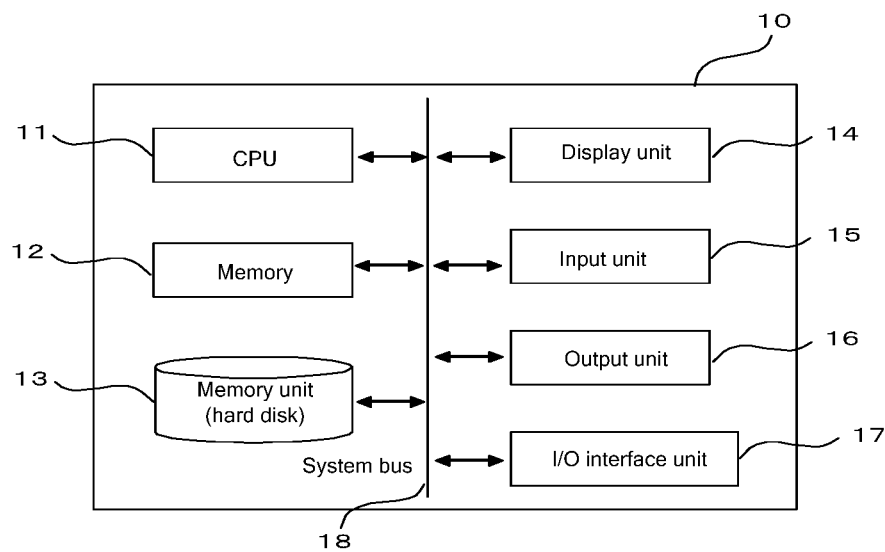
FIG. 6 is a structural example of the disclosed calculation device of an acid dissociation constant.

A structural example of the disclosed calculation device of an acid dissociation constant is illustrated in FIG. 6.

For example, the calculation device 10 of an acid dissociation constant is composed by connecting CPU 11 (calculation unit), a memory 12, a memory unit 13, a display unit 14, an input unit 15, an output unit 16, an I/O interface unit 17, etc. via a system bus 18.

The central processing unit (CPU) 11 is configured to perform calculation (e.g., four arithmetic operation, relational operation, etc.), and control of operations of hardware and software.

The memory 12 is a memory, such as a random access memory (RAM), and a read only memory (ROM). The RAM is configured to store an operation system (OS) and application programs read from the ROM and the memory unit 13, and function as a main memory and work area of the CPU 11.

The memory unit 13 is a device for storing various programs and data. For example, the memory unit 13 is a hard disk. In the memory unit 13, programs to be executed by the CPU 11, data required for executing the programs, and an OS are stored.

The program is stored in the memory unit 13, loaded on the RAM (a main memory) of the memory 12, and executed by the CPU 11.

The display unit 14 is a display device. For example, the display unit is a display device, such as a CRT monitor, and a liquid crystal panel.

The input unit 15 is an input device for various types of data. Examples of the input unit include a key board, and a pointing device (e.g., a mouse).

The output unit 16 is an output device for various types of data. For example, the output unit is a printer.

The I/O interface unit 17 is an interface for connecting to various external devices. For example, the I/O interface unit enables input and output of data of CD-ROMs, DVD-ROMs, MO disks, and USB memory sticks.

Figure 7:
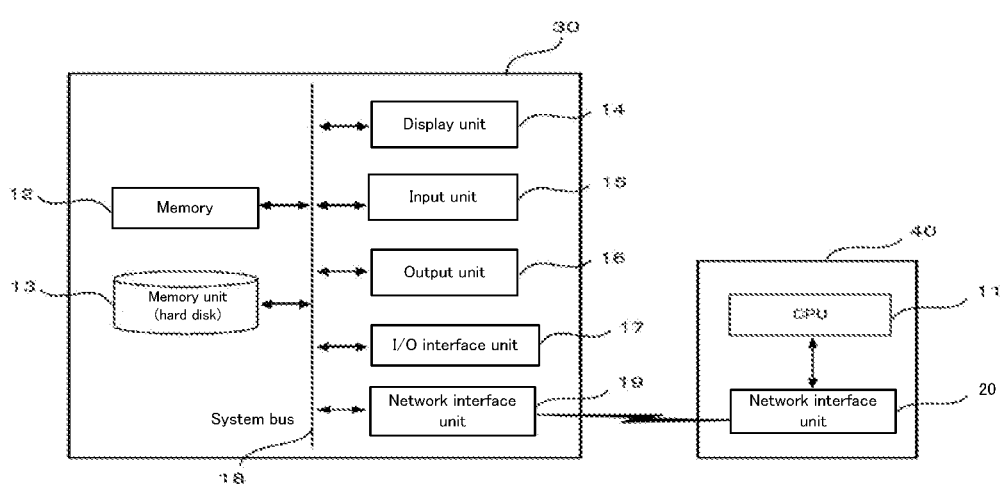
FIG. 7 is another structural example of the disclosed calculation device of an acid dissociation constant.

Another structural example of the disclosed calculation device of an acid dissociation constant is illustrated in FIG. 7.

The structural example of FIG. 7 is a structural example of a cloud-type calculation device, where a CPU 11 is independent from a memory unit 13. In the structural example, a computer 30 storing therein the memory unit 13 and a computer 40 storing therein the CPU 11 are coupled with each other through network interface units 19 and 20.

The network interface units 19 and 20 are hardware configured to communicate using the internet.

Figure 8:
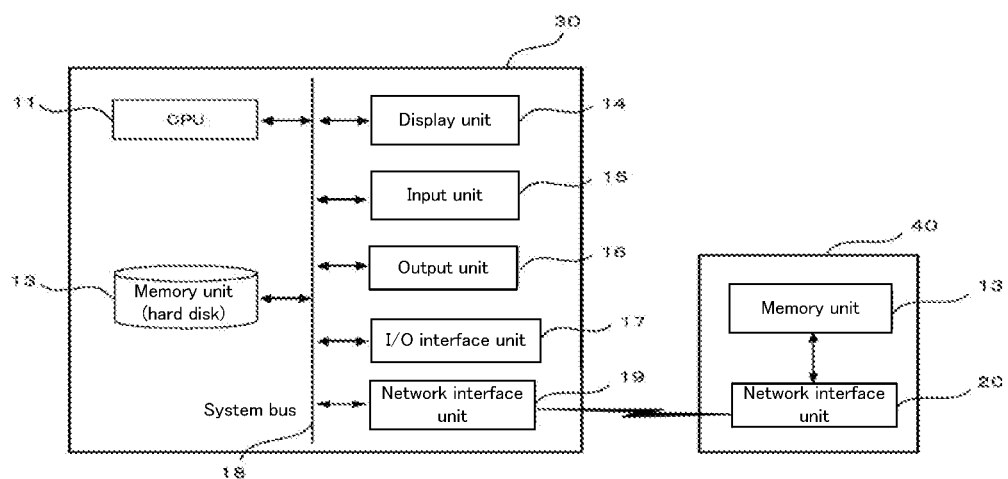
FIG. 8 is another structural example of the disclosed calculation device of an acid dissociation constant.

Yet another example of the disclosed calculation device of an acid dissociation constant is illustrated in FIG. 8.

The structural example of FIG. 8 is a structural example of a cloud-type calculation device, where a memory unit 13 is independent from CPU 11. In the structural example, a computer 30 storing therein the CPU 11 and a computer 40 storing therein the memory unit 13 are coupled with each other through network interface units 19 and 20.

According to the technology of Japanese Patent Application Laid-Open (JP-A) No. 2014-157020, a highly accurate result of proton association from OH can be obtained regardless of a type of a molecule. However, pKa estimation accuracy decreases in case of proton dissociation from amine.

The disclosed embodiments aim to solve the above-described various problems existing in the art, and to achieve the following object. Specifically, the present disclosure has an object to provide a calculation method of an acid dissociation constant, a calculation device of an acid dissociation constant, and a program for calculating an acid dissociation constant, all of which is associated with an estimation value of pKa, can be applied for a macromolecule, screening of a large volume of data, and a novel molecule synthesized, and do not decrease accuracy in an estimation value even in calculation of amine.

The disclosed calculation method of an acid dissociation constant can solve the above-described various problems existing in the art, can achieve the above-mentioned object, can be applied for macromolecules associated with estimation values of pKa and can be applied for screening of a large volume of data and novel molecules synthesized, and does not lower accuracy of estimation values even in calculation for amine.

The disclosed program can solve the above-described various problems existing in the art, can achieve the above-mentioned object, can be applied for macromolecules associated with estimation values of pKa and can be applied for screening of a large volume of data and molecules newly synthesized, and does not lower accuracy of estimation values even in calculation for amine.

The disclosed calculation device of an acid dissociation constant can solve the above-described various problems existing in the art, can achieve the above-mentioned object, can be applied for macromolecules associated with estimation values of pKa and can be applied for screening of a large volume of data and molecules newly synthesized, and does not lower accuracy of estimation values even in calculation for amine.

EXAMPLES

The disclosed technology is explained hereinafter, but Examples below shall not be construed as to limit the scope of the disclosed technology.

Example 1, Comparative Example 1, and Comparative Example 2

In Example and Comparative Examples below, estimation values of pKa of 133 types of molecules whose measured values of pKa had been known were determined. Then, the correlation between the measured values and the estimation values was confirmed.

Example 1

Figure 9:
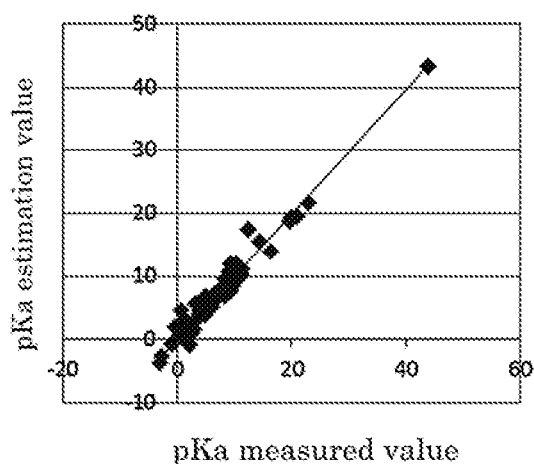
FIG. 9 is a graph depicting the results of Example 1.

An estimation value of pKa was determined using the disclosed technology. Then, correlation between the measured values and the estimation values were confirmed. The results are presented in Table 2 and FIG. 9.

Note that, for the calculation of the estimation value, FUJITSU Technical Computing Solution SCIGRESS available from FUJITSU LIMITED was used and a calculation value calculated by RM1 method (semi-empirical molecular orbital method) was used.

The mathematical equation (4) was used for the calculation of the estimation value.

Comparative Example 1

Figure 10:
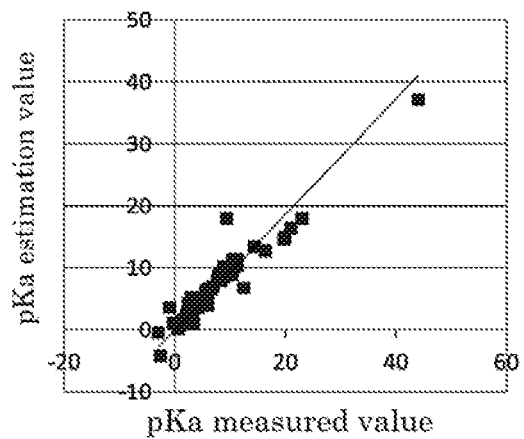
FIG. 10 is a graph depicting the results of Comparative Example 1.

An estimation value of pKa was determined by using marvin Sketch that was known to have high accuracy in pKa estimation and was available from ChemAxon. Then, correlation between the measured values and the estimation values were confirmed. The results are presented in Table 2 and FIG. 10.

Comparative Example 2

Figure 11:
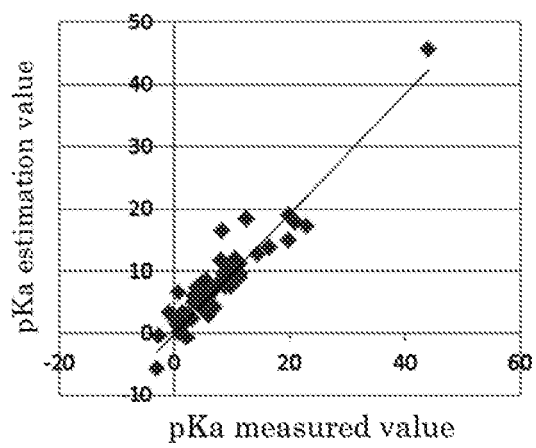
FIG. 11 is a graph depicting the results of Comparative Example 2.

An estimation value of pKa was determined using the technology disclosed in Japanese Patent Application Laid-Open (JP-A) No. 2014-157020. Then, correlation between the measured values and the estimation values were confirmed. The results are presented in Table 2 and FIG. 11.

Note that, for the calculation of the estimation value, FUJITSU Technical Computing Solution SCIGRESS available from FUJITSU LIMITED was used and a calculation value calculated by RM1 method (semi-empirical molecular orbital method) was used.

The 133 types of the molecules used in the pKa estimation calculations in Example 1, Comparative Example 1, and Comparative Example 2 are presented in Tables 1-1 to 1-23.

TABLE 1-1

| Number | pKa | Name | Structure (circle: dissociation point) |
|---|---|---|---|
| 1 | 9.98 | NH3C2H4NH2 | |
| 2 | 8.12 | NH3NH2 | |
| 3 | −0.88 | NH3NH3 | |
| 4 | 5.97 | NH3OH | |
| 5 | 9.69 | alanine | |
| 6 | 9.69 | allylamine | |

TABLE 1-2

| Number | pKa | Name | Structure (circle: dissociation point) |
|---|---|---|---|
| 7 | 8.78 | allyldimethylamine | |
| 8 | 10.11 | allylmethylamine | |
| 9 | 9.21 | ammonia | |

TABLE 1-2-continued

| Number | pKa | Name | Structure (circle: dissociation point) |
|---|---|---|---|
| 10 | 9.04 | arginine | |
| 11 | 12.48 | arginine | |

TABLE 1-3

| Number | pKa | Name | Structure (circle: dissociation point) |
|---|---|---|---|
| 12 | 8.8 | asparagine | |
| 13 | 9.82 | aspartic acid | |
| 14 | 9.34 | benzylamine | |
| 15 | 9.68 | benzylethylamine | |
| 16 | 9.58 | benzylmethylamine | |

TABLE 1-4

| Number | pKa | Name | Structure (circle: dissociation point) |
|---|---|---|---|
| 17 | 10.64 | cyclohexylamine | |
| 18 | 10.49 | cyclohexyl-methylamine | |
| 19 | 2.97 | DABCO | |
| 20 | 8.82 | DABCO | |
| 21 | 11.25 | di-n-butylamine | |
| 22 | 11 | di-n-propylamine | |
| 23 | 11.01 | di-sec-butylamine | |

TABLE 1-5

| Number | pKa | Name | Structure (circle: dissociation point) |
|---|---|---|---|
| 24 | 9.29 | diallylamine | |
| 25 | 8.79 | diallylmethylamine | |
| 26 | 8.9 | diethanolamine | |
| 27 | 10.98 | diethylamine | |
| 28 | 10.5 | di-isobutylamine | |
| 29 | 11.05 | di-isopropylamine | |
| 30 | 9.91 | dimethyl isobutylamine | |

TABLE 1-6

| Number | pKa | Name | Structure (circle: dissociation point) |
|---|---|---|---|
| 31 | 10.3 | dimethyl isopropylamine | |
| 32 | 10.02 | dimethyl n-butylamine | |
| 33 | 9.99 | dimethyl n-propylamine | |
| 34 | 10.4 | dimethyl sec-butylamine | |
| 35 | 10.52 | dimethyl t-butylamine | |
| 36 | 10.64 | dimethylamine | |
| 37 | 9.99 | dimethylethylamine | |
| 38 | 9.5 | ethanolamine | |
| 39 | 10.63 | ethylamine | |

TABLE 1-7

| Number | pKa | Name | Structure (circle: dissociation point) |
|---|---|---|---|
| 40 | 9.13 | glutamine | |
| 41 | 9.67 | glutamic acid | |
| 42 | 9.6 | glycine | |
| 43 | 9.17 | histidine | |

TABLE 1-8

| Number | pKa | Name | Structure (circle: dissociation point) |
|---|---|---|---|
| 44 | 9.68 | isoleusine | |
| 45 | 10.63 | isopropylamine | |
| 46 | 9.6 | leucine | |

TABLE 1-8-continued

| Number | pKa | Name | Structure (circle: dissociation point) |
|---|---|---|---|
| 47 | 8.95 | lysine | |

TABLE 1-9

| Number | pKa | Name | Structure (circle: dissociation point) |
|---|---|---|---|
| 48 | 10.53 | lysine | |
| 49 | 4.6 | methoxyamine | |
| 50 | 10.64 | methylamine | |
| 51 | 8.36 | morpholine | |
| 52 | 7.78 | n-benzoylpiperazine | |
| 53 | 10.59 | n-butylamine | |
| 54 | 8.28 | n-carbethoxypiperazine | |

TABLE 1-10

| Number | pKa | Name | Structure (circle: dissociation point) |
|---|---|---|---|
| 55 | 5.96 | n-methylhydroxylamine | —NH₂⊕—OH |
| 56 | 4.75 | n-methylmethoxyamine | —NH₂⊕—O— |
| 57 | 10.53 | n-propylamine | NH₃⊕-propyl |
| 58 | 10.21 | neo-pentylamine | NH₃⊕-neopentyl |
| 59 | 9.13 | phenylalanine | H₃N⊕-CH(CH₂Ph)-COO⁻ |
| 60 | 10.49 | phenylamylamine | NH₃⊕-(CH₂)₅-Ph |

TABLE 1-11

| Number | pKa | Name | Structure (circle: dissociation point) |
|---|---|---|---|
| 61 | 10.4 | phenyl-butylamine | NH₃⊕-(CH₂)₄-Ph |
| 62 | 9.83 | phenyl-ethylamine | NH₃⊕-(CH₂)₂-Ph |
| 63 | 10.2 | phenyl-propylamine | NH₃⊕-(CH₂)₃-Ph |
| 64 | 5.33 | piperazine | H₂N⊕···NH₂⊕ (piperazine diprotonated) |

TABLE 1-11-continued

| Number | pKa | Name | Structure (circle: dissociation point) |
|---|---|---|---|
| 65 | 9.73 | piperazine | H₂N⊕···NH (piperazine monoprotonated) |
| 66 | 11.22 | piperidine | H₂N⊕ (piperidine) |
| 67 | 10.6 | proline | H₂N⊕-pyrrolidine-COOH |

TABLE 1-12

| Number | pKa | Name | Structure (circle: dissociation point) |
|---|---|---|---|
| 68 | 11.3 | pyrrolidine |  |
| 69 | 44 | pyrrolidine | 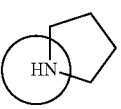 |
| 70 | 11 | quinuclidine |  |
| 71 | 10.56 | sec-butylamine | 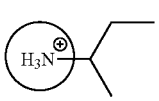 |
| 72 | 9.15 | serine | 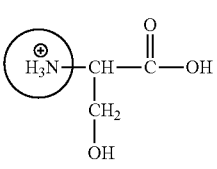 |
| 73 | 10.55 | t-butylamine | 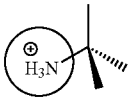 |
| 74 | 11.23 | t-butylcyclohexylamine | 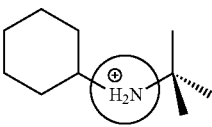 |

TABLE 1-13

| Number | pKa | Name | Structure (circle: dissociation point) |
|---|---|---|---|
| 75 | 9.1 | threonine | 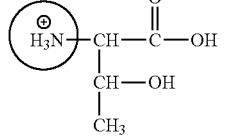 |
| 76 | 10.89 | tri-n-butylamine | 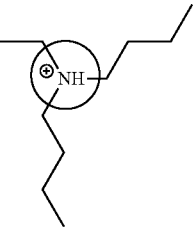 |
| 77 | 10.65 | tri-n-propylamine | 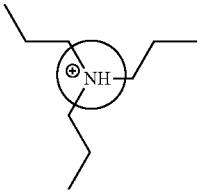 |
| 78 | 8.31 | triallylamine | 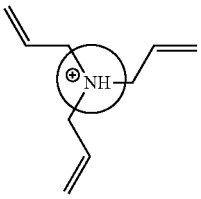 |

TABLE 1-14

| Number | pKa | Name | Structure (circle: dissociation point) |
|---|---|---|---|
| 79 | 7.8 | triethanolamine | 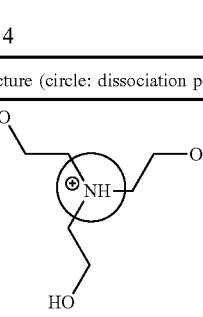 |
| 80 | 10.65 | triethylamine | 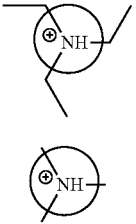 |
| 81 | 9.76 | trimethylamine |  |
| 82 | 9.39 | tryptophan | 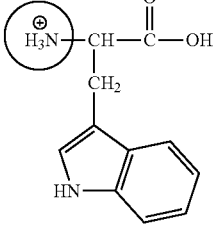 |
| 83 | 9.11 | tyrosine | 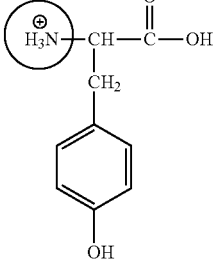 |

TABLE 1-15

| Number | pKa | Name | Structure (circle: dissociation point) |
|---|---|---|---|
| 84 | 9.62 | valine | |
| 85 | 9.3 | 1,2,3-triazole | |
| 86 | 2.2 | 1,2,4-triazole | |
| 87 | 10.3 | 1,2,4-triazole | |
| 88 | 3.39 | 1,8-naphthyridine | |
| 89 | 3.92 | 1-naphtylamine | |
| 90 | 3.3 | 2-methoxypyridine | |

TABLE 1-16

| Number | pKa | Name | Structure (circle: dissociation point) |
|---|---|---|---|
| 91 | 6 | 2-methylpyridine | |
| 92 | 4.16 | 2-naphthalamine | |
| 93 | −0.3 | 2-cyanopyridine | |
| 94 | −2.6 | 2-nitropyridine | |
| 95 | 4.5 | 2-phenylpyridine | |
| 96 | 4.9 | 3-methoxypyridine | |

TABLE 1-17

| Number | pKa | Name | Structure (circle: dissociation point) |
|---|---|---|---|
| 97 | 5.7 | 3-methylpyridine | |
| 98 | 1.4 | 3-cyanopyridine | |
| 99 | 0.6 | 3-nitropyridine | |
| 100 | 4.8 | 3-phenylpyridine | |
| 101 | 6.6 | 4-methoxypyridine | |

TABLE 1-17-continued

| Number | pKa | Name | Structure (circle: dissociation point) |
|---|---|---|---|
| 102 | 6 | 4-methylpyridine | |

TABLE 1-18

| Number | pKa | Name | Structure (circle: dissociation point) |
|---|---|---|---|
| 103 | 1.9 | 4-cyanopyridine | |
| 104 | 1.6 | 4-nitropyridine | |
| 105 | 5.5 | 4-phenylpyridine | |
| 106 | 5.15 | 5,6-benzoquinoline | |
| 107 | 4.25 | 7,8-benzoquinoline | |

TABLE 1-19

| Number | pKa | Name | Structure (circle: dissociation point) |
|---|---|---|---|
| 108 | 0.78 | Ph2NH2 | |
| 109 | 5.2 | PhNHMe2 | |
| 110 | 5.6 | acridine | |
| 111 | 4.6 | aniline | |
| 112 | 16.4 | benzimidazole | |
| 113 | 5.05 | benzoquinoline | |

TABLE 1-20

| Number | pKa | Name | Structure (circle: dissociation point) |
|---|---|---|---|
| 114 | 19.9 | carbazole | |
| 115 | 6 | histidine | |
| 116 | 6.9 | imidazole | |
| 117 | 14.4 | imidazole | |

TABLE 1-20-continued

| Number | pKa | Name | Structure (circle: dissociation point) |
|---|---|---|---|
| 118 | 21 | indole | |
| 119 | 4.9 | indoline | |

TABLE 1-21

| Number | pKa | Name | Structure (circle: dissociation point) |
|---|---|---|---|
| 120 | 5.14 | isoquinoline | |
| 121 | −3 | isoxazole | |
| 122 | 0.8 | oxazole | |
| 123 | 2.5 | purine | |
| 124 | 8.9 | purine | |
| 125 | 0.6 | pyrazine | |
| 126 | 19.8 | pyrazole | |

TABLE 1-22

| Number | pKa | Name | Structure (circle: dissociation point) |
|---|---|---|---|
| 127 | 2.3 | pyridazine | |
| 128 | 5.2 | pyridine | |
| 129 | 1.3 | pyrimidine | |
| 130 | 23 | pyrrole | |
| 131 | 4.92 | quinoline | |

TABLE 1-23

| Number | pKa | Name | Structure (circle: dissociation point) |
|---|---|---|---|
| 132 | 5 | tetrahydroquinoline | |
| 133 | 4.9 | tetrazole | |

TABLE 2

| | Correlation coefficient | Standard error |
|---|---|---|
| Ex. 1 | 0.96 | 1.0 |
| Comp. Ex. 1 | 0.90 | 1.5 |
| Comp. Ex. 2 | 0.86 | 1.9 |

As it could be also confirmed from Table 2, it was confirmed that Example 1 could perform estimation of high accuracy on amines compared to Comparative Examples 1 and 2.

Note that, the disclosed technology can also perform estimation on oxoacid as highly accurate as Comparative Example 2.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the sprit and scope of the invention.

What is claimed is:

1. A calculation method of an acid dissociation constant of a calculation target molecule that includes at least one amino group including a nitrogen atom and a hydrogen atom in dissociation of a hydrogen atom from the at least one amino group, the calculation method comprising:
by a computer,
selecting, from among atoms of the calculation target molecule, sets of two atoms including a first set (HN) of the hydrogen atom (H) and a nitrogen atom (N) directly bonded to the hydrogen atom, a second set (NX) of the nitrogen atom and another atom (X) (with the proviso that the hydrogen atom is excluded) directly bonded to the first atom, and a third set (HX) of the hydrogen atom (H) and the another atom (X); and
calculating the acid dissociation constant of the calculation target molecule that includes the at least one amino group in dissociation of the hydrogen atom from the at least one amino group, with the selected first, second, and third sets, using following functions:

$$pK_3 \cong f\left(\sum_X a_{NX}B_{NX}, \sum_X a_{HX}B_{HX},\right.$$

$$\left. a_R R_{NH} + a_E E_{MO} + a_D\left(\sum_{i,j\in N} D_{ij}^2 - \sum_X B_{NX}\right)\right), \text{ and}$$

$$D_{Nfree} = \sum_{i,j\in N} D_{ij}^2 - \sum_X B_{NX}$$

$D_{Nfree}$ function,
that use,
an index value (B) determined based on first electron density between a set of two atoms, among the sets of two atoms, of the calculation target molecule,
a coefficient value (a) determined based on types of two elements of the set of the two atoms,
a second electron density ($D_{Nfree}$) of the nitrogen atom (N) in the amino group where the second electron density ($D_{Nfree}$) is not related to a bond between the nitrogen atom and the another atom (X),
a bond distance (R) between the nitrogen atom (N) and the hydrogen atom, and
molecular orbital energy ($E_{MO}$) of the calculation target molecule, and
wherein in the $D_{Nfree}$ function, $D_{ij}$ represents elements (electron density matrix) with which a nitrogen atom directly bonded to a target proton among the electron density, i represents a line component of the electron density matrix and j represents a column component of the electron density matrix,
to thereby reduce computational complexity of the calculation of the acid dissociation constant.

2. The calculation method according to claim 1,
wherein the coefficient value is set for each hydrogen atom (H) of the first set (HN) of the hydrogen atom (H) and the nitrogen atom (N), the second set (NX) being plural second sets of the nitrogen atom (N) and the another atom (X) where a number of the second set (NX) is a number of types of elements of the another atom (X), and the third set (HX) being plural third sets (HXs) of the hydrogen atom (H) and the another atom (X) where a number of the third sets (HSx) is a number of types of elements of the another atom (X).

3. The calculation method according to claim 1,
wherein the product of the index value and the coefficient value is used in the functions.

4. The calculation method according to claim 1,
wherein the second electron density ($D_{Nfree}$), the bond distance (R), and the molecular orbital energy ($E_{MO}$) form a linear combination in the functions.

5. The calculation method according to claim 1,
wherein the molecular orbital energy ($E_{MO}$) is energy of a highest occupied molecular orbital of the calculation target molecule or energy of a lowest unoccupied molecular orbital of the calculation target molecule.

6. A calculation device of an acid dissociation constant, comprising:
a memory; and
a processor coupled to the memory, wherein,
the processor is configured to calculate an acid dissociation constant of a calculation target molecule that includes at least one amino group including a nitrogen atom and a hydrogen atom in dissociation of a hydrogen atom from the at least one amino group,
the memory includes, as data,
an index value (B) determined based on first electron density between a set of two atoms, from among atoms, of the calculation target molecule,
a coefficient value (a) determined based on types of two elements of the set of the two atoms,
a second electron density ($D_{Nfree}$) of a nitrogen atom (N) in the one amino group where the second electron density ($D_{Nfree}$) is not related to a bond between the nitrogen atom and another atom (X),
a bond distance (R) between the nitrogen atom and the hydrogen atom, and
molecular orbital energy of the calculation target molecule, and
wherein the processor is configured to,
select, from among atoms of the calculation target molecule, sets of two atoms including a first set (HN) of the hydrogen atom (H) and a nitrogen atom (N) directly bonded to the hydrogen atom, a second set (NX) of the nitrogen atom (N) and another atom (X) (with the proviso that the hydrogen atom is excluded) directly bonded to the first atom, and a third set (HX) of the hydrogen atom (H) and the another atom (X); and
calculate the acid dissociation constant of the calculation target molecule that includes the at least one amino group in dissociation of the hydrogen atom from the at least one amino group, with the selected first, second, and third sets, using following functions stored in the memory:

$$pK_3 \cong f\left(\sum_X a_{NX}B_{NX}, \sum_X a_{HX}B_{HX},\right.$$

$$a_R R_{NH} + a_E E_{MO} + a_D \left( \sum_{i,j \in N} D_{ij}^2 - \sum_X B_{NX} \right), \text{ and}$$

$$D_{Nfree} = \sum_{i,j \in N} D_{ij}^2 - \sum_X B_{NX}$$

$D_{Nfree}$ function,
that use,
the index value (B), the coefficient value (a), the second electron density ($D_{Nfree}$), the bond distance (R), and the molecular orbital energy ($E_{MO}$), and
wherein in the $D_{Nfree}$ function, $D_{ij}$ represents elements (electron density matrix) with which a nitrogen atom directly bonded to a target proton among the electron density, i represents a line component of the electron density matrix and j represents a column component of the electron density matrix,
to thereby reduce computational complexity of the calculation of the acid dissociation constant.

7. The calculation device according to claim 6,
wherein the coefficient value is set for each hydrogen atom (H) of the first set (HN) of the hydrogen atom (H) and the nitrogen atom (N), the second set (NX) being plural second sets of the nitrogen atom (N) and the another atom (X) where a number of the second set (NX) is a number of types of elements of the another atom (X), and the third set (HX) being plural third sets (HXs) of the hydrogen atom (H) and the another atom (X) where a number of the third sets (HSx) is a number of types of elements of the another atom (X).

8. The calculation device according to claim 6,
wherein the product of the index value and the coefficient value is calculated in the processor.

9. The calculation device according to claim 8,
wherein the processor is configured to form a linear combination with the second electron density ($D_{Nfree}$), the bond distance (R), and the molecular orbital energy ($E_{MO}$).

10. The calculation device according to claim 6,
wherein the molecular orbital energy ($E_{MO}$) is energy of a highest occupied molecular orbital of the calculation target molecule or energy of a lowest unoccupied molecular orbital of the calculation target molecule.

\* \* \* \* \*